(12) United States Patent
Khalaj et al.

(10) Patent No.: US 10,675,441 B2
(45) Date of Patent: Jun. 9, 2020

(54) ECHOGENIC COIL MEMBER FOR A CATHETER ASSEMBLY

(71) Applicant: Avent, Inc., Alpharetta, GA (US)

(72) Inventors: Steve S. Khalaj, Laguna Hills, CA (US); John Anthony Rotella, San Diego, CA (US); Justin Jeffrey Coker, Laguna Niguel, CA (US)

(73) Assignee: Avent, Inc., Alpharetta, GA (US)

( * ) Notice: Subject to any disclaimer, the term of this patent is extended or adjusted under 35 U.S.C. 154(b) by 235 days.

(21) Appl. No.: 15/735,719

(22) PCT Filed: Jun. 18, 2015

(86) PCT No.: PCT/US2015/036363
§ 371 (c)(1),
(2) Date: Dec. 12, 2017

(87) PCT Pub. No.: WO2016/204759
PCT Pub. Date: Dec. 22, 2016

(65) Prior Publication Data
US 2018/0169383 A1    Jun. 21, 2018

(51) Int. Cl.
*A61M 25/01* (2006.01)
*A61M 25/00* (2006.01)
(Continued)

(52) U.S. Cl.
CPC ......... *A61M 25/0108* (2013.01); *A61B 8/481* (2013.01); *A61M 25/007* (2013.01);
(Continued)

(58) Field of Classification Search
CPC ............ A61M 25/0108; A61M 25/007; A61M 25/0012; A61M 25/0068; A61B 8/481;
(Continued)

(56) References Cited

U.S. PATENT DOCUMENTS 4,697,595 A   10/1987  Breyer et al.
4,969,890 A   11/1990  Sugita et al.
(Continued)

FOREIGN PATENT DOCUMENTS

EP    2 343 098 A1    7/2011
EP    2 540 336 A1    1/2013
(Continued)

OTHER PUBLICATIONS

International Search Report for PCT/US2015/036363, dated Feb. 22, 2016, 4 pages.
(Continued)

*Primary Examiner* — Amber R Stiles
(74) *Attorney, Agent, or Firm* — Dority & Manning, P.A.

(57) ABSTRACT

The present invention is directed to an echogenic coil member for a catheter assembly and methods of manufacturing same. The catheter assembly includes a catheter having a proximal end and a distal end that defines a lumen extending from the proximal end to the distal end. Thus, the echogenic coil member is configured within the lumen of the catheter. Further, the coil member includes a plurality of outwardly extending projections that contain a plurality of discontinuities. As such, the discontinuities are configured to enhance ultrasonic imaging of the catheter assembly.

17 Claims, 7 Drawing Sheets

(51) Int. Cl.
*A61B 8/08* (2006.01)
*A61B 90/00* (2016.01)

(52) U.S. Cl.
CPC .... *A61M 25/0012* (2013.01); *A61M 25/0068* (2013.01); *A61B 2090/378* (2016.02); *A61B 2090/3782* (2016.02); *A61B 2090/3925* (2016.02)

(58) Field of Classification Search
CPC .... A61B 2090/3925; A61B 2090/3782; A61B 2090/378
See application file for complete search history.

(56) References Cited

U.S. PATENT DOCUMENTS

| | | | |
|---|---|---|---|
| 5,081,997 | A | 1/1992 | Bosley, Jr. et al. |
| 5,759,154 | A | 6/1998 | Hoyns |
| 6,179,809 | B1 * | 1/2001 | Khairkhahan .... A61M 25/0084 604/528 |
| 7,438,711 | B2 | 10/2008 | Deniega et al. |
| 7,465,291 | B2 | 12/2008 | Massengale |
| 7,527,609 | B2 | 5/2009 | Deniega et al. |
| 7,569,045 | B2 | 8/2009 | Deniega et al. |
| 8,328,771 | B2 | 12/2012 | Massengale |
| 8,611,993 | B2 | 12/2013 | Vitullo et al. |
| 8,652,098 | B2 | 2/2014 | Haslinger |
| 8,796,908 | B2 | 8/2014 | Okuba |
| 9,802,025 | B2 | 10/2017 | Khalaj |
| 2002/0142119 | A1 | 10/2002 | Seward et al. |
| 2004/0077948 | A1 | 4/2004 | Violante et al. |
| 2004/0116896 | A1 | 6/2004 | Massengale |
| 2004/0193109 | A1 | 9/2004 | Prestidge et al. |
| 2004/0249288 | A1 | 12/2004 | Ichikawa |
| 2007/0167739 | A1 | 7/2007 | Salo |
| 2008/0058702 | A1 * | 3/2008 | Arndt ................. A61B 8/0833 604/20 |
| 2009/0131910 | A1 | 5/2009 | Webler |
| 2011/0172542 | A1 * | 7/2011 | Racz ................. A61M 25/0012 600/463 |
| 2011/0319758 | A1 * | 12/2011 | Wang ................. A61B 17/3403 600/439 |
| 2012/0059308 | A1 | 3/2012 | Hsu et al. |
| 2012/0095404 | A1 | 4/2012 | Massengale et al. |
| 2012/0126663 | A1 | 5/2012 | Jenninger et al. |
| 2013/0223702 | A1 | 8/2013 | Holsing et al. |
| 2014/0024928 | A1 | 1/2014 | Boctor et al. |
| 2014/0142509 | A1 | 5/2014 | Bonutti et al. |
| 2014/0316327 | A1 | 10/2014 | Rajendran et al. |
| 2014/0378841 | A1 | 12/2014 | Coats et al. |
| 2015/0038378 | A1 | 2/2015 | Cheng et al. |

FOREIGN PATENT DOCUMENTS

| | | |
|---|---|---|
| JP | 2001293091 A | 10/2001 |
| JP | 2010279546 A | 12/2010 |
| WO | WO 99/51294 | 10/1999 |
| WO | WO 00/04287 | 7/2000 |
| WO | WO 2009/091514 A2 | 7/2009 |
| WO | WO 2014/174305 A2 | 10/2014 |

OTHER PUBLICATIONS

Stephen M. Klein, M.D., et al., "Piezoelectric Vibrating Needle and Catheter for Enhancing Ultrasound-Guided Peripheral Nerve Blocks", Technical Communication from the International Anesthesia Research Society, vol. 105, No. 6, Dec. 2007, 3 pages.
Co-pending U.S. Appl. No. 15/735,731, filed Dec. 12, 2017.
Co-pending U.S. Appl. No. 15/743,900, filed Jan. 11, 2018.

* cited by examiner

ECHOGENIC COIL MEMBER FOR A CATHETER ASSEMBLY

RELATED APPLICATIONS

The present application claims priority to International Application Number PCT/US2015/036363 filed on Jun. 18, 2015, which is incorporated herein in its entirety by reference hereto.

FIELD OF THE INVENTION

The present invention relates generally to echogenic devices and more particularly to an echogenic coil member for a catheter assembly that can be inserted into a medium such as biological tissue and imageable with sonic imaging equipment.

BACKGROUND

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. The types of devices which are surgically sterilized and inserted into patients are many. Typical examples include: needles, catheters and a variety of other medical products such as stents, dilators, pacing leads, introducers, angiography devices, angioplasty devices, pacemakers, in-patient appliances such as pumps and other devices. Various approaches have been used to enhance ultrasonic imaging by modifying the reflective surface characteristics of these devices.

U.S. Pat. No. 5,081,997 to Bosley, Jr. et al, for "Echogenic Devices, Material and Method" discloses a device such as a needle that includes an interface having a shape that is formed with a dimension that is less than a wavelength of the incident sonic beam. According to Bosley, Jr. et al., the shape includes a dimension such as a radius of curvature which is much less than the wavelength of the sonic beam. The interface may include the outside surface a device or article or material. That surface has a plurality of partially spherical discontinuities for producing a scattered component of the image in response to the incident beam. This image is produced regardless of the incident beam angle of which conventional devices depend for producing a reflected or constructive interference image. The scattered component of the image is produced when the radius of the partially spherical discontinuities or a dimension of another geometric shape or surface are much less than the wavelength of the incoming sonic beam.

U.S. Patent Application Publication No. 2004/0249288 A1 to Ichikawa for "Ultrasonic Puncture Needle" discloses a device including an array of doughnut shaped recesses having a center portion remaining as a protrusion. According to U.S. Publication No. 2004/0249288 A1, the recesses are also formed with faces, bottoms and sides being generally flat so to obtain reflection echoes with a great intensity for the incident ultrasonic waves with a shallow incident angle.

While the approaches described in U.S. Pat. No. 5,081,997 and U.S. Publication No. 2004/0249288 A1 have shown promise, improvements have been sought that would result in an echogenic catheter that provides enhanced ultrasonic imaging, in a manner that is inexpensive to manufacture, and simple and reliable to use.

Accordingly, the present disclosure is directed to an echogenic coil member for a catheter assembly that provides enhanced ultrasonic imaging.

SUMMARY OF THE INVENTION

Objects and advantages of the invention will be set forth in part in the following description, or may be obvious from the description, or may be learned through practice of the invention.

In one aspect, the present invention is directed to an echogenic catheter assembly. The catheter assembly includes a catheter having a proximal end and a distal end that defines a lumen extending from the proximal end to the distal end. Further, the catheter assembly includes a coil member configured within the lumen of the catheter. The coil member includes a plurality of outwardly extending projections that contain a plurality of discontinuities. As such, the discontinuities are configured to enhance ultrasonic imaging of the catheter assembly.

In one embodiment, the plurality of discontinuities may be located at a distal region of coil member, e.g. at a distal tip of the coil member.

In certain embodiments, at least a portion of the coil member may be in a compressed position such that adjacent outwardly extending projections of the compressed portion contact each other. Thus, in such embodiments, one or more discontinuities of contacting adjacent outwardly extending projections may connect to form a larger discontinuity.

In alternative embodiments, at least a portion of the coil member may be in an expanded position such that adjacent outwardly extending projections of the expanded portion are spaced apart from each other. As such, one or more discontinuities of spaced-apart outwardly extending projections are also spaced apart from each other.

In further embodiments, the coil member may be sized to fit within the lumen of the catheter, e.g. such that the coil member can be easily inserted therethrough. In alternative embodiments, the coil member may be embedded into an interior wall of the catheter.

In particular embodiments, the discontinuities may include any one of or combination of the following: indentations, grooves, notches, recesses, threads, protrusions, or similar. More specifically, in certain embodiments, the discontinuities may be laser-etched into the coil member. In additional embodiments, the coil member may be constructed of any suitable material, e.g. a metal or metal alloy. For example, in certain embodiments, the metal or metal alloy may include at least one of or a combination of the following: aluminum, titanium, copper, tin, nickel, zinc, magnesium, stainless steel, or similar.

In still further embodiments, the catheter may include a closed distal tip and one or more infusion holes. Thus, the infusion holes are configured to allow a medication flowing through the lumen of the catheter to exit therethrough.

In alternative embodiments, the catheter assembly may further include a needle configured within a lumen of the coil member. For example, in certain embodiments, the catheter assembly may be an over-the-needle (OTN) catheter assembly. In such an embodiment, the distal end of the catheter may include an open distal tip. Thus, the needle may be configured to extend past the open distal tip.

In another aspect, the present disclosure is directed to a method for manufacturing an echogenic catheter assembly. More specifically, the method includes providing a catheter having a lumen that extends from a proximal end to a distal end thereof. Another step includes etching a plurality of discontinuities onto a wire member. The method also includes coiling the wire member so as to form a coil member having a plurality of outwardly extending projections, wherein the plurality of discontinuities are exposed on an outer surface of the plurality of outwardly extending projections so as to enhance ultrasonic imaging of the catheter assembly. The method also includes inserting the coil member into the lumen of the catheter.

In yet another aspect, the present disclosure is directed to a method for manufacturing an echogenic catheter assembly. More specifically, the method includes providing a catheter having a lumen that extends from a proximal end to a distal end thereof. Another step includes coiling a wire member so as to form a coil member having a plurality of outwardly extending projections. The method also includes forming a plurality of discontinuities onto an outer surface of the outwardly extending projections so as to enhance ultrasonic imaging of the catheter assembly. A further step includes inserting the coil member into the lumen of the catheter.

In one embodiment, the method may also include forming the plurality of discontinuities onto a distal region of the outer surface of the outwardly extending projections. In another embodiment, the method may also include compressing at least a portion of the coil member such that adjacent outwardly extending projections of the compressed portion contact each other. Thus, in such an embodiment, the method may also include forming one or more discontinuities onto the outer surface of contacting adjacent outwardly extending projections to form one or more larger discontinuities.

In alternative embodiments, the method may include expanding at least a portion of the coil member such that adjacent outwardly extending projections of the expanded portion are spaced apart from each other. Thus, in such an embodiment, the method may also include forming one or more discontinuities onto the outer surface of the spaced-apart adjacent outwardly extending projections.

Further, in certain embodiments, the method may include laser-etching the plurality of discontinuities onto the outer surface of the outwardly extending projections. It should also be understood that the coil member and associated discontinuities may be configured according to the any of the embodiments as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Generally, the present disclosure is directed to an echogenic coil member for a catheter assembly and methods of manufacturing same. The catheter assembly includes a catheter having a proximal end and a distal end that defines a lumen extending from the proximal end to the distal end. As such, the coil member may be configured within the lumen of the catheter. More specifically, the coil member includes a plurality of outwardly extending projections that contain a plurality of discontinuities on an outer surface thereof. Thus, the discontinuities are configured to enhance ultrasonic imaging of the catheter assembly.

Figure 1:
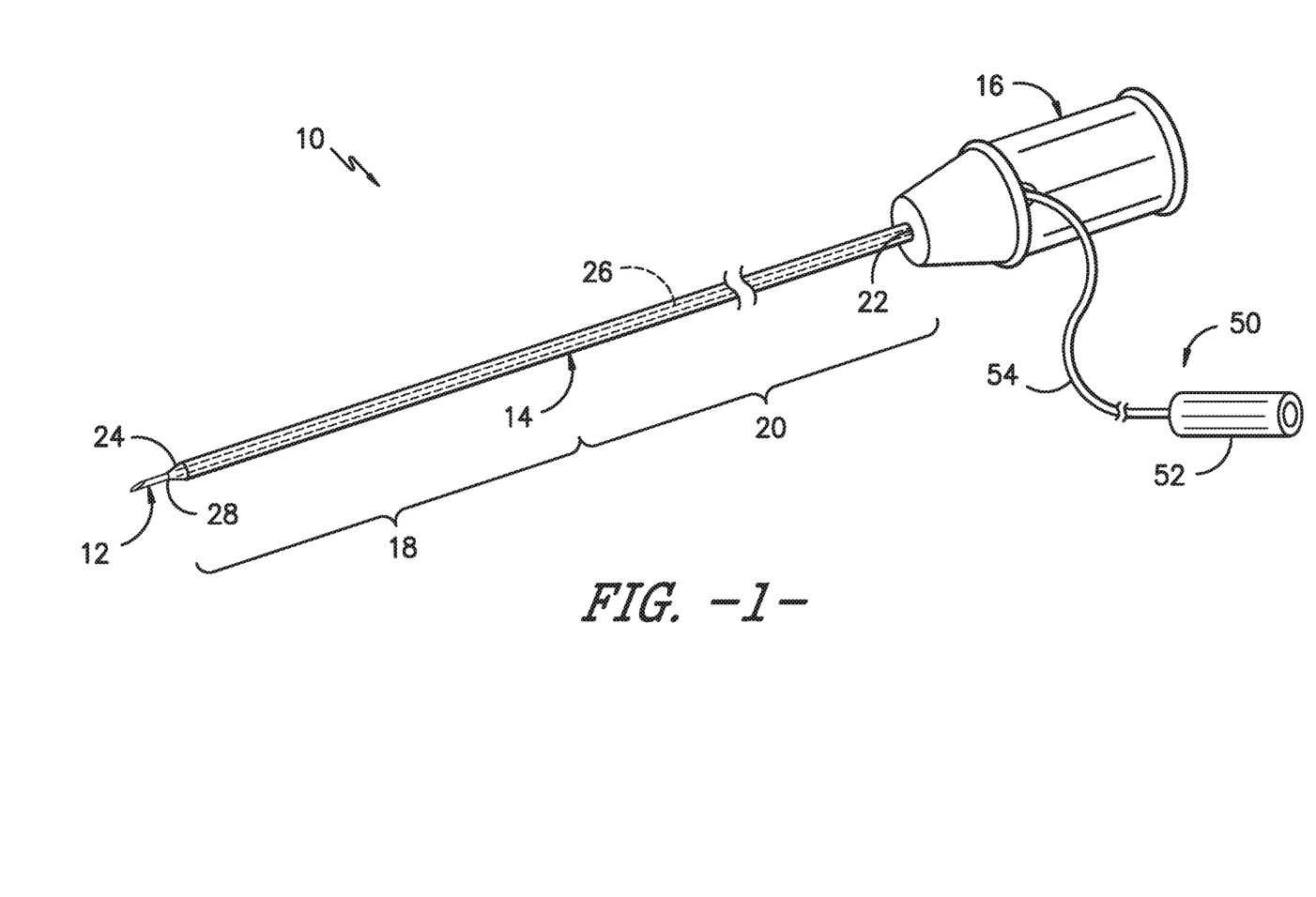
FIG. 1 illustrates a perspective view of one embodiment of an echogenic catheter assembly according to the present disclosure.
Figure 2:
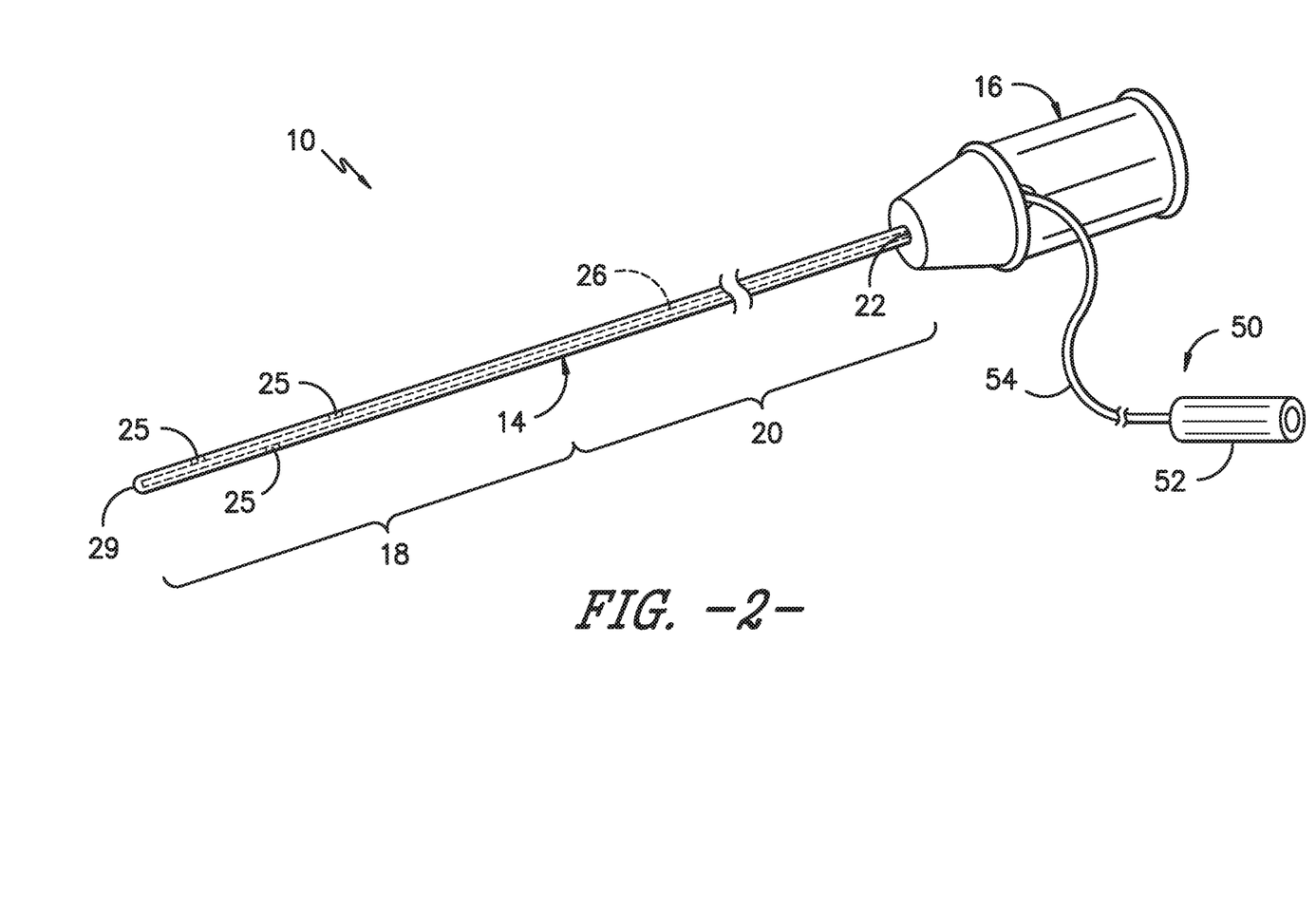
FIG. 2 illustrates a perspective view of another embodiment of an echogenic catheter assembly according to the present disclosure.

Referring now to the drawings, FIGS. 1 and 2 illustrate various embodiments of an echogenic catheter assembly 10 according to the present disclosure. For example, as shown, the catheter assembly 10 includes a catheter 14 having a proximal end 22 and a distal end 24 coaxially mounted onto a needle 12. In certain embodiments, as shown in FIG. 1, the catheter assembly 10 may be an over-the-needle (OTN) catheter assembly, i.e. the catheter 14 is coaxially mounted to the needle 12. Thus, the catheter assembly 10 may be configured such that the catheter 14 and needle 12 can be simultaneously inserted into a patient. In addition, the catheter 14 (and/or the needle 12) defines a lumen 26 extending from the proximal end 22 to the distal end 24 of the catheter 14. Thus, the catheter 14 is configured to deliver a treatment fluid to a targeted site within the patient via the lumen 26. More specifically, as shown in FIG. 1, the catheter assembly 10 may include an open distal tip 28 such that the needle 12 may extend beyond the open distal tip 28. In addition, the proximal end 22 of the catheter 14 may include a hub 16 configured thereon for mating communication with a fluid delivery device (not shown) such that a treatment fluid can be delivered to a targeted site within a patient via the lumen 26 and the open distal tip 28 of the catheter 14. The fluid delivery device may be any suitable device known in the art, such as a pump, reservoir, syringe, or the like. Further, the hub 16 may have any conventional configuration, such as a Luer-lock fitting.

Figure 5:
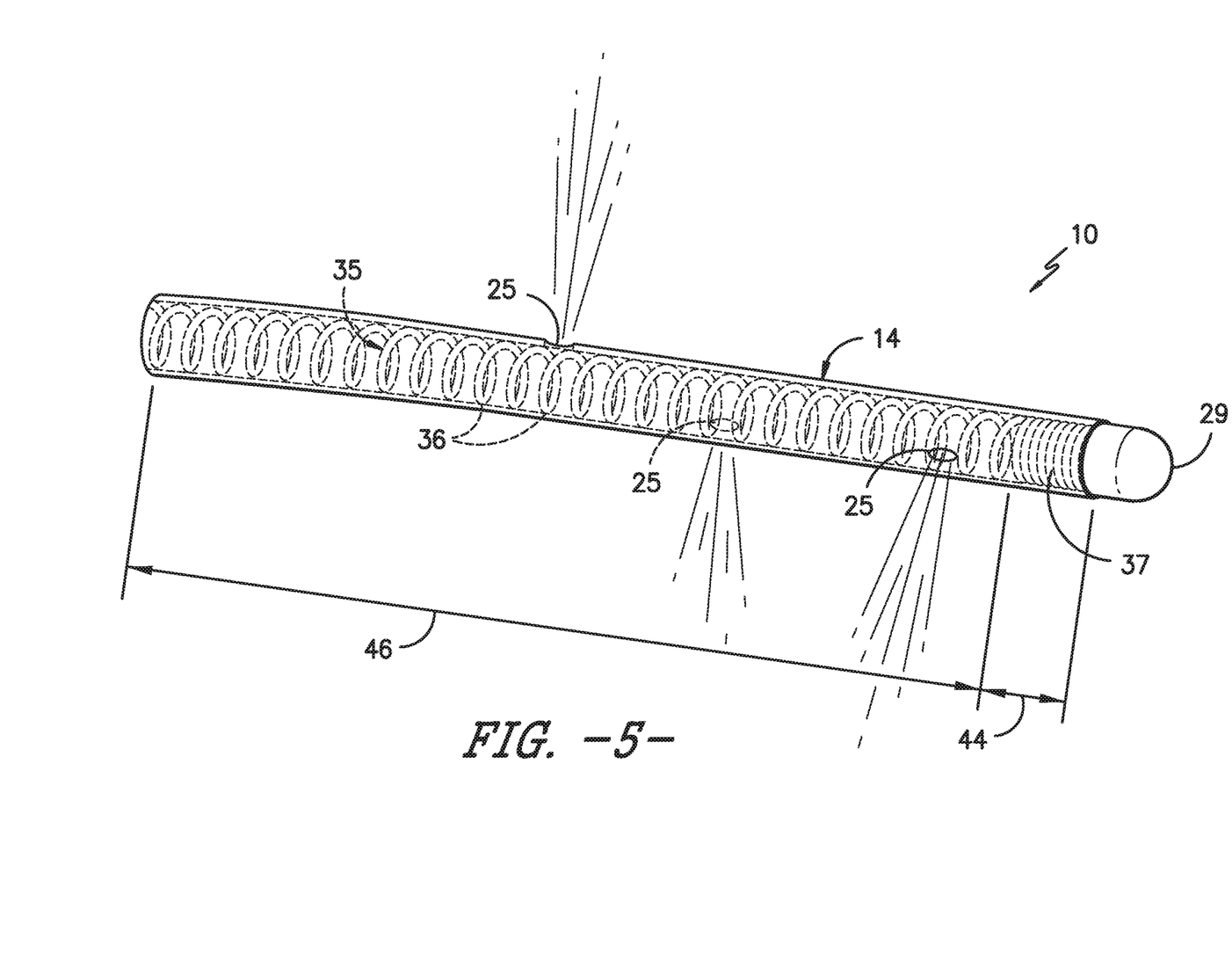
FIG. 5 illustrates a side view one embodiment of an echogenic catheter assembly according to the present disclosure, particularly illustrating a coil member configured within a lumen of a catheter of the catheter assembly.

In additional embodiments, as shown in FIGS. 2 and 5, the catheter assembly 10 may include a closed distal tip 29, e.g. depending on the desired delivery application of the treatment fluid to the patient. More specifically, as shown, the catheter assembly 10 may include a closed distal tip 29 without the needle 12. In such an embodiment, the catheter 14 may contain one or more infusion holes 25 configured to deliver a treatment fluid to a targeted site within a patient via the lumen 26 of the catheter 14. In addition, it should also be understood that the OTN catheter assemblies as described herein may optional include one or more infusion holes in addition to the open distal tip 28 for administering a treatment fluid to a patient.

Still referring to FIGS. 1 and 2, the echogenic catheter assembly 10 may also include a heat application assembly 50 configured to apply heat to the catheter 14. For example, as shown, the heat application assembly 50 may be coupled with the hub 16 of the catheter 14 so as to apply heat or current to the catheter 14. In further embodiments, the heat application assembly 50 may be directly coupled to the catheter 14 (or the needle 12 where applicable) or any other suitable component of the catheter assembly 10, e.g. the wire and/or coil members 30, 35 as described herein. Further, the heat application assembly 50 may correspond to a nerve stimulator apparatus having a nerve stimulator 52 that provides heat or current through one or more stimulator wires 54. It should be understood, however, that the heat application assembly 50 can further include any other suitable heating assembly known in the art and the illustrated embodiment is provided for illustrative purposes only. For example, in further embodiments, the heat application assembly 50 may also include one or more battery devices, temperature-controlled water, an ultrasound device, a vibration device, or similar.

As shown generally in FIGS. 3-10, the echogenic catheter assembly 10 also includes an echogenic wire member 30 or an echogenic coil member 35 configured to enhance ultrasonic imaging of the catheter assembly 10. In addition, the wire and/or coil members 30, 35 are configured to provide support to the catheter 14 as the catheter 14 is being inserted within a patient and/or during a medical procedure. Thus, in certain embodiments, the nerve stimulator apparatus 50 (FIG. 1) may be configured to apply current through the wire and/or coil members 30, 35 for use during various medical procedures.

Figure 3:
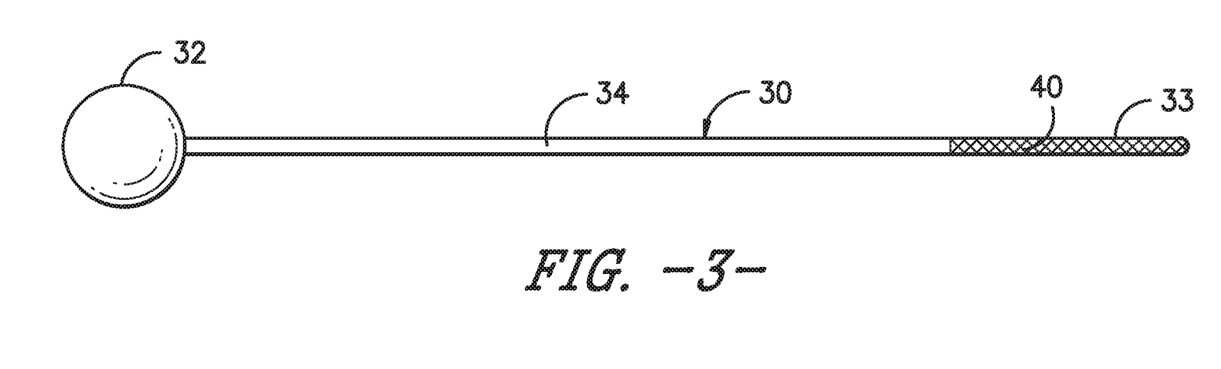
FIG. 3 illustrates a side view of one embodiment of a wire member of a catheter assembly according to the present disclosure.
Figure 4:
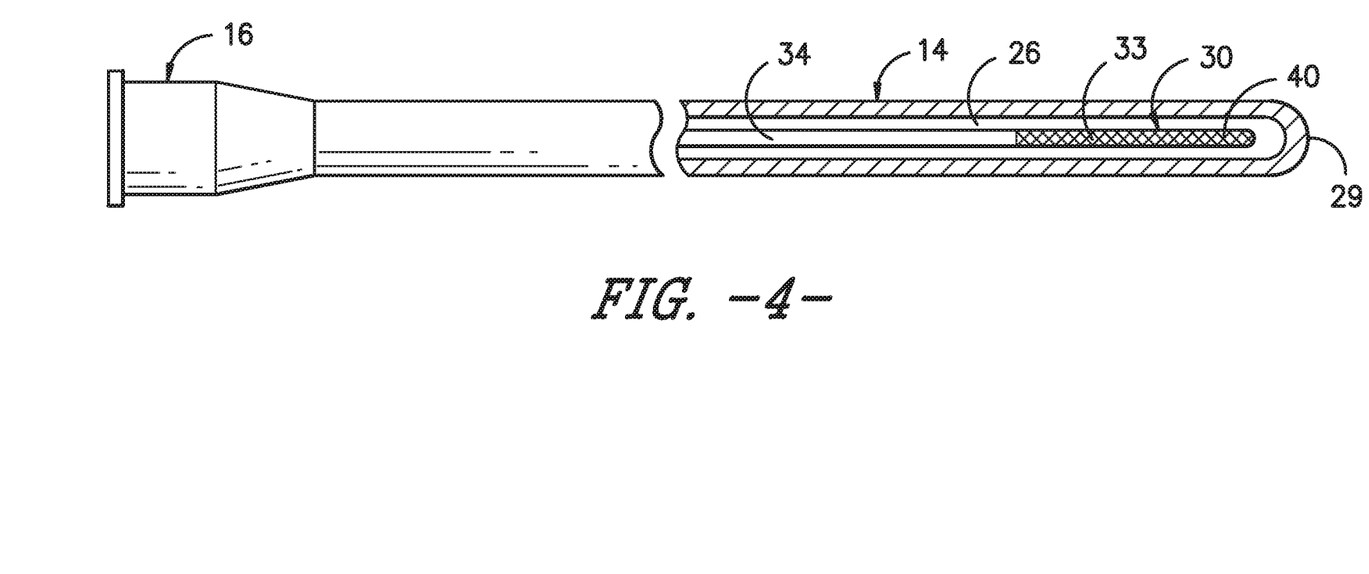
FIG. 4 illustrates a side view of one embodiment of a wire member configured within a lumen of a catheter of a catheter assembly according to the present disclosure, particularly illustrating a distal region of the wire member having a plurality of discontinuities.

Referring particularly to FIGS. 3 and 4, the wire member 30 or stylet defines an outer surface 34 extending from a proximal end 32 to a distal end 33. Further, as shown, the distal end 33 of the wire member 30 may include one or more discontinuities configured to enhance ultrasonic imaging of the catheter assembly 10. More specifically, as shown, the distal end 33 of the wire member 30 may include one or more laser-etched discontinuities 40 that enhance ultrasonic imaging of the catheter assembly 10.

Referring now to FIGS. 5-9, the echogenic catheter assembly 10 may also include an echogenic coil member 35 configured to enhance ultrasonic imaging of the catheter assembly 10. More specifically, as shown in FIG. 5, the coil member 35 may include one or more discontinuities 40 that are configured to enhance ultrasonic imaging of the catheter assembly 10. Further, as shown, the coil member 35 may be sized to fit within the lumen 26 of the catheter, e.g. such that the coil member 35 can be easily inserted therethrough. Alternatively, the coil member 35 may be embedded into an interior wall of the catheter 14. More specifically, as shown, the coil member 35 may be completely embedded within the interior wall of the lumen 26 of the catheter 14 such that the internal diameter of the catheter 14 remains unchanged and the needle 12 (if present) can easily fit therethrough. In alternative embodiments, the coil member 35 may be partially embedded within the interior wall of the catheter 14 of the lumen 26 of the catheter 14.

Referring particularly to FIGS. 6-9, the coil member 35 includes a plurality of outwardly extending projections 36 that contain the plurality of discontinuities 40 on an outer surface 38 thereof. For example, as shown, the discontinuities 40 may be located at a distal region of the coil member 35, e.g. at a distal end 37 of the coil member 35. In further embodiments, the discontinuities 40 may be located at any suitable location along a length of the coil member 35.

Figure 6:
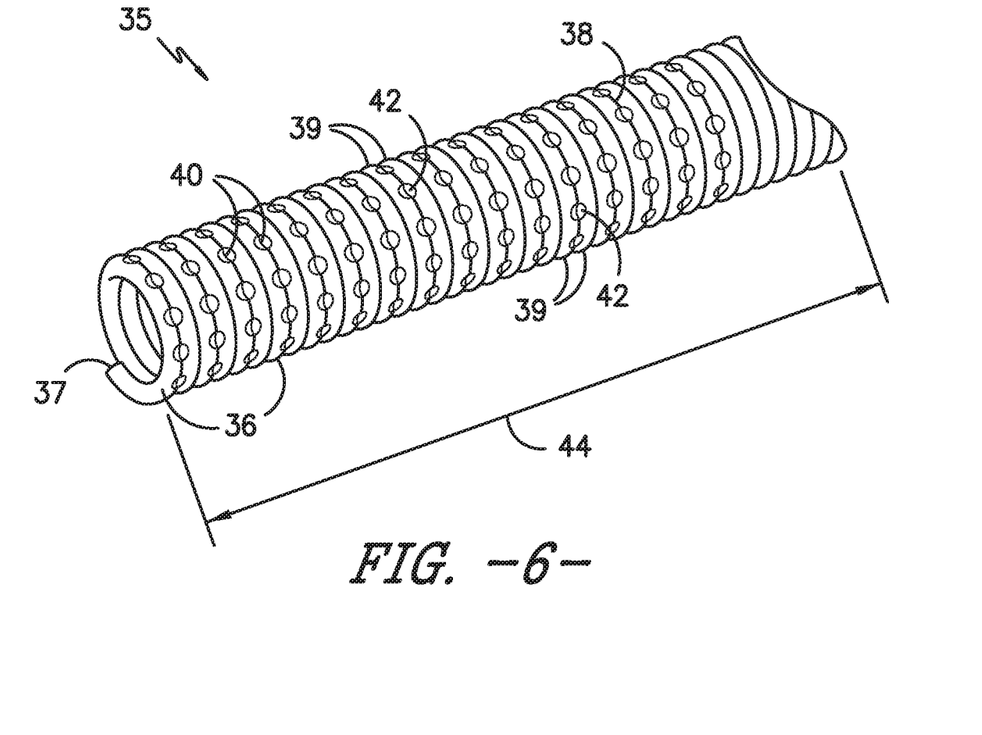
FIG. 6 illustrates a detailed, perspective view one embodiment of a compressed portion of a coil member of a catheter assembly according to the present disclosure, particularly illustrating a distal region of the coil member having a plurality of discontinuities.
Figure 7:
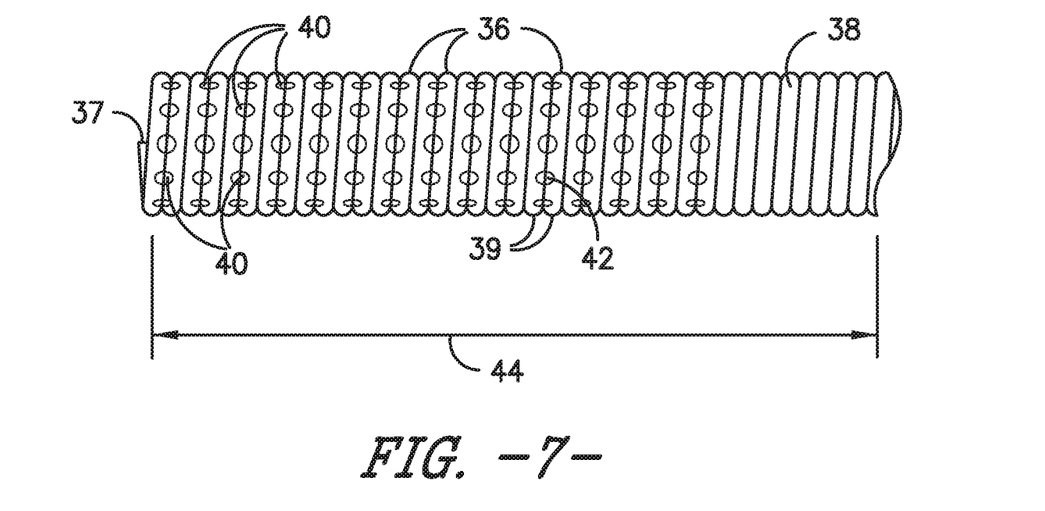
FIG. 7 illustrates a side view the coil member of FIG. 6.
Figure 8:
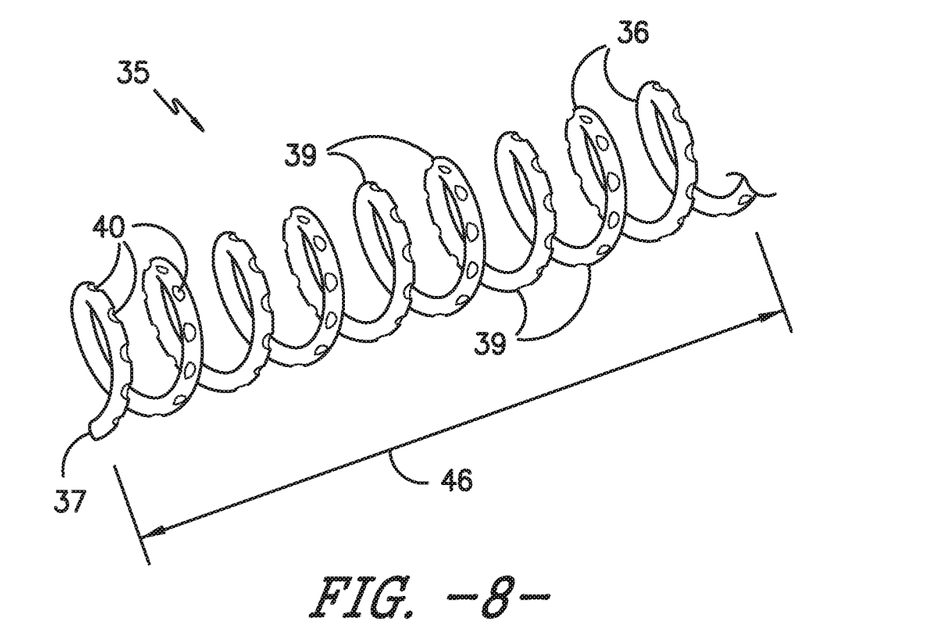
FIG. 8 illustrates a detailed, perspective view one embodiment of an expanded portion of a coil member of a catheter assembly according to the present disclosure, particularly illustrating a distal region of the coil member having a plurality of discontinuities.
Figure 9:
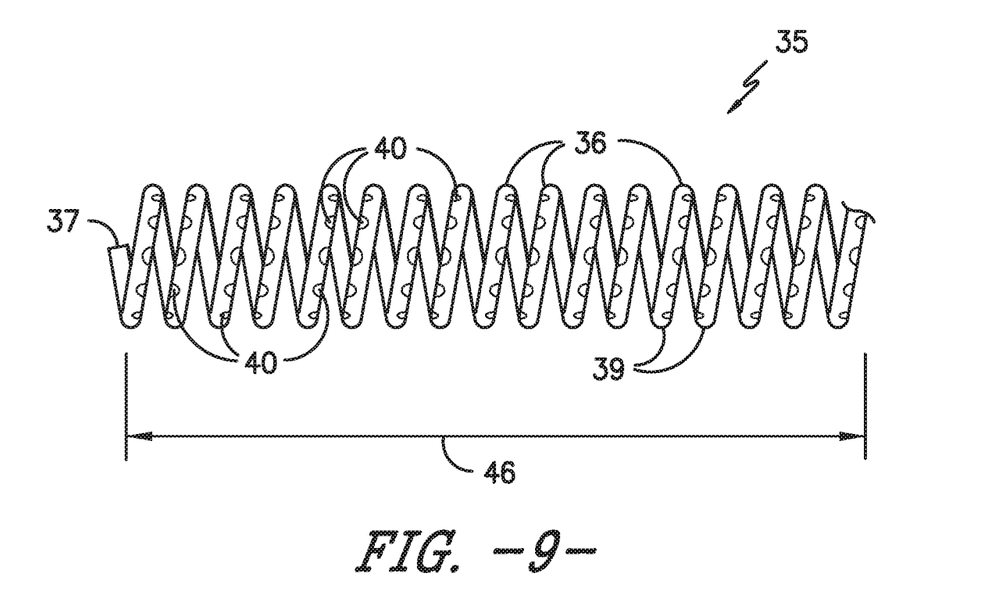
FIG. 9 illustrates a side view the coil member of FIG. 8.

In addition, as shown in FIGS. 5-7, at least a portion of the coil member 35 may be in a compressed position 44 such that adjacent outwardly extending projections 39 of the compressed portion 44 contact each other. Thus, as shown in FIGS. 6 and 7, one or more discontinuities 40 of contacting adjacent outwardly extending projections 39 may connect to form a larger discontinuity 42. In alternative embodiments, as shown in FIGS. 5 and 8-9, at least a portion of the coil member 35 may be in an expanded position 46 such that adjacent outwardly extending projections 39 of the expanded portion 46 are spaced apart from each other. As such, one or more discontinuities 40 of spaced-apart outwardly extending projections 39 are also spaced apart from each other. In further embodiments, the compressed and extended portions of the coil member 35 may contain one or more discontinuities 40.

In additional embodiments, the discontinuities 40 of the echogenic wire or coil members 30, 35 may include any suitable discontinuities having any suitable size and/or shape arranged in any suitable pattern so as to provide enhanced ultrasonic imagine. For example, in certain embodiments, the discontinuities 40 may include at least one or more of the following: indentations, grooves, notches, recesses, threads, protrusions, or similar. Further, in certain embodiments, the discontinuities 40 may be arranged in a predetermined pattern so as to enhance ultrasonic imaging of the catheter assembly 10. In one embodiment, for example, the predetermined pattern may include organized rows and/or columns of discontinuities. Alternatively, the pattern of discontinuities 40 may be random. More particularly, in certain embodiments, the discontinuities 40 may have a generally round shape with flat bottoms and flat sides. In further embodiments, the discontinuities 40 may include a first spherical indentation and a second spherical indentation contained within the first indentation to enhance ultrasonic imaging, e.g. as described in U.S. Patent Application Publication No.: 2014/0378841 entitled "Echogenic Article with Compound Discontinuities" filed on Jun. 18, 2014, which is herein incorporated by reference in its entirety.

In further embodiments, the discontinuities 40 of the echogenic wire or coil members 30, 35 may be manufactured using any suitable means. For example, in certain embodiments, the discontinuities 40 may be manufactured using laser etching, spatter techniques (i.e. displacement of metal and/or other phenomena), cutting, machining, or similar.

In additional embodiments, the wire or coil members 30, 35 may be constructed of any suitable echogenic material. For example, in specific embodiments, the echogenic wire or coil members 30, 35 may be constructed of a metal or a metal alloy. More particularly, the metal or metal alloy may include at least one of or a combination of the following: aluminum, titanium, copper, tin, nickel, zinc, magnesium, stainless steel, or similar.

Figure 10:
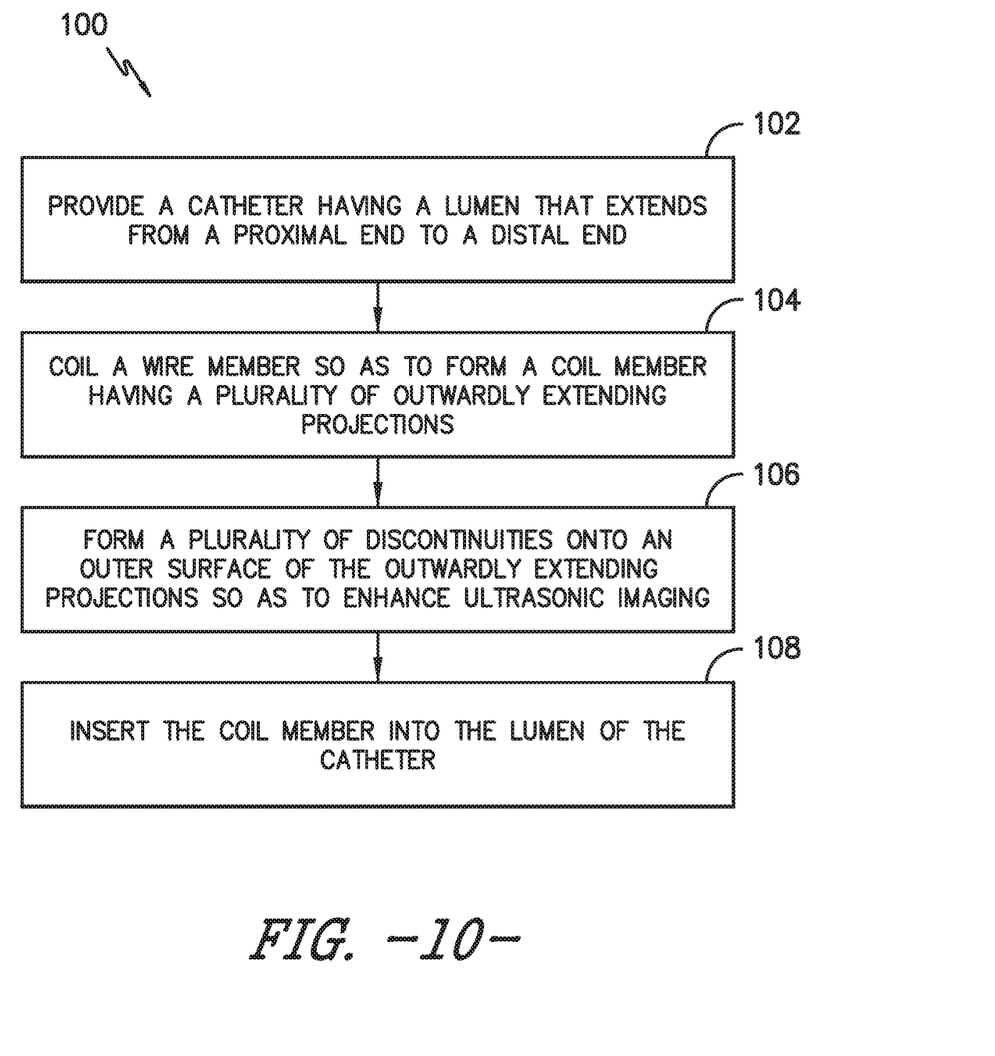
FIG. 10 illustrates a flow diagram of one embodiment of manufacturing an echogenic catheter assembly according to the present disclosure.

Referring now to FIG. 10, a flow diagram of one embodiment of a method 100 for manufacturing an echogenic catheter assembly 10 according to the present disclosure is illustrated. As shown at 102, the method 100 includes providing a catheter 14 that defines a lumen 26 extending from a proximal end 22 to a distal end 24 thereof. As shown at 104, the method 100 includes coiling a wire member 30 so as to form a coil member 35 having a plurality of outwardly extending projections 36. As shown at 106, the method 100 includes forming a plurality of discontinuities 40 onto an outer surface 38 of the outwardly extending projections 36 so as to enhance ultrasonic imaging of the catheter assembly 10. As shown at 108, the method 100 includes inserting the coil member 35 into the lumen 26 of the catheter 14 so as to form the catheter assembly 10. In addition, it should be understood that the method steps as described herein may be performed in any suitable order. For example, in additional embodiments, the discontinuities 40 may be formed onto the wire member 30 before the wire member 30 is formed into the coil member 35.

In further embodiments, the method 100 may also include forming the plurality of discontinuities 40 onto a distal region of the outer surface 38 of the outwardly extending projections 36. In additional embodiments, the method 100 may include compressing at least a portion of the coil member 35 such that adjacent outwardly extending projections 36 of the compressed position 44 contact each other. Thus, the method 100 may also include forming one or more discontinuities 40 onto the outer surface 38 of contacting adjacent outwardly extending projections 39 to form one or more larger discontinuities 42. More specifically, in certain embodiments, the method 100 may include laser etching one or more discontinuities 40 onto the outer surface 38 of contacting adjacent outwardly extending projections 39.

In alternative embodiments, the method 100 may also include expanding at least a portion of the coil member such that adjacent outwardly extending projections 39 of the expanded portion 46 are spaced apart from each other. Thus, the method 100 may also include forming one or more discontinuities 40 onto the outer surface 38 of the spaced-apart adjacent outwardly extending projections 39.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An echogenic catheter assembly, comprising:
    a catheter comprising a proximal end and a distal end and defining a lumen extending from the proximal end to the distal end; and,
    a coil member configured within the lumen of the catheter, the coil member forming a plurality of outwardly extending projections, the outwardly extending projections comprising a plurality of discontinuities configured to enhance ultrasonic imaging of the coil member,
    wherein at least a portion of the coil member is in a compressed position such that adjacent outwardly extending projections of the compressed portion contact each other,
    wherein each of the plurality of discontinuities comprise an elliptical shape formed on the exterior surface of the body of the echogenic band, and wherein one or more of the plurality of discontinuities of contacting adjacent outwardly extending projections connect to form a larger discontinuity.

2. The catheter assembly of claim 1, wherein the plurality of discontinuities are located at a distal region of coil member.

3. The catheter assembly of claim 1, wherein at least a portion of the coil member is in an expanded position such that adjacent outwardly extending projections of the expanded portion are spaced apart from each other.

4. The catheter assembly of claim 1, wherein the coil member is embedded into an interior wall of the catheter.

5. The catheter assembly of claim 1, wherein the discontinuities comprises at least one or more of the following: indentations, grooves, notches, recesses, threads, or protrusions.

6. The catheter assembly of claim 1, wherein the discontinuities are laser-etched into the coil member.

7. The catheter member of claim 1, wherein the coil member is constructed of a metal or metal alloy, wherein the metal or metal alloy comprises at least one of or a combination of the following: aluminum, titanium, copper, tin, nickel, zinc, magnesium, or stainless steel.

8. The catheter assembly of claim 1, wherein the catheter comprises a closed distal tip and one or more infusion holes, and wherein the infusion holes allow a medication flowing through the lumen of the catheter to exit therethrough.

9. The catheter assembly of claim 1, further comprising a needle configured within a lumen of the coil member.

10. The catheter assembly of claim 9, wherein the distal end of the catheter comprises an open distal tip, and wherein the needle is configured to extend past the open distal tip.

11. A method for manufacturing an echogenic catheter assembly, the method comprising:
    providing a catheter defining a lumen that extends from a proximal end to a distal end thereof;
    etching a plurality of discontinuities onto a wire member, each of the plurality of discontinuities comprising an elliptical shape;
    coiling the wire member so as to form a coil member having a plurality of outwardly extending projections;
    compressing at least a portion of the coil member to form a compressed portion of the coil member, wherein adjacent outwardly extending projections of the compressed portion contact each other, wherein the plurality of discontinuities are exposed on an outer surface of the plurality of outwardly extending projections and extend across contacting adjacent outwardly extending projections to form one or more larger discontinuities so as to enhance ultrasonic imaging; and, inserting the coil member into the lumen of the catheter.

12. A method for manufacturing an echogenic catheter assembly, the method comprising:

providing a catheter having a lumen that extends from a proximal end to a distal end thereof;

coiling a wire member so as to form a coil member having a plurality of outwardly extending projections;

compressing at least a portion of the coil member to form a compressed portion of the coil member, wherein adjacent outwardly extending projections of the compressed portion contact each other;

forming a plurality of discontinuities onto an outer surface of contacting adjacent outwardly extending projections of the compressed portion to form one or more larger discontinuities and to enhance ultrasonic imaging; and, inserting the coil member into the lumen of the catheter.

13. The method of claim 12, further comprising forming the plurality of discontinuities onto a distal region of the outer surface of the plurality of outwardly extending projections.

14. The method of claim 12, further comprising:

expanding at least a portion of the coil member such that adjacent outwardly extending projections of the expanded portion are spaced apart from each other, and forming one or more discontinuities onto the outer surface of the spaced-apart adjacent outwardly extending projections.

15. The method of claim 12, wherein the plurality of discontinuities comprises at least one or more of the following: indentations, grooves, notches, recesses, threads, or protrusions.

16. The method of claim 12, further comprising laser-etching the plurality of discontinuities onto the outer surface of the plurality of outwardly extending projections.

17. The method of claim 12, wherein the coil member is constructed of a metal or metal alloy, wherein the metal or metal alloy comprises at least one of or a combination of the following: aluminum, titanium, copper, tin, nickel, zinc, magnesium, or stainless steel.

* * * * *